United States Patent [19]

Kawakita et al.

[11] 4,397,853

[45] Aug. 9, 1983

[54] ISOXAZOLE DERIVATIVES

[75] Inventors: Takeshi Kawakita; Tomio Muro; Michihide Setoguchi, all of Nakatsu, Japan

[73] Assignee: Yoshitomi Pharmaceutical Industries Ltd., Japan

[21] Appl. No.: 253,930

[22] PCT Filed: Nov. 25, 1980

[86] PCT No.: PCT/JP80/00286

§ 371 Date: Jul. 28, 1981

§ 102(e) Date: Apr. 14, 1981

[87] PCT Pub. No.: WO81/01554

PCT Pub. Date: Jun. 11, 1981

[30] Foreign Application Priority Data

Nov. 28, 1979 [JP] Japan ............................ 54-154715

[51] Int. Cl.³ .................. A61K 31/495; C07D 471/20
[52] U.S. Cl. ..................................... 424/250; 424/251; 424/263; 424/267; 424/272; 544/300; 544/344; 546/187; 546/193; 546/194; 546/199; 546/209; 546/256; 546/275; 546/17; 546/20; 548/240; 548/247

[58] Field of Search ............... 544/344, 300; 548/240, 548/247; 546/193, 194, 187, 17, 20, 199, 209, 256, 275; 424/263, 267, 251, 250, 272

[56] References Cited

U.S. PATENT DOCUMENTS 3,890,323 6/1975 Yamamoto et al. ................ 544/344

FOREIGN PATENT DOCUMENTS 1386546 12/1964 France ............................... 546/209

Primary Examiner—Robert T. Bond
Attorney, Agent, or Firm—Larson and Taylor

[57] ABSTRACT

Isoxazole derivatives represented by the formula

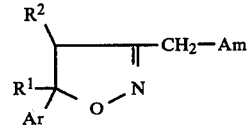

wherein Ar, $R^1$, $R^2$ and Am are as defined in the specification, or salts thereof. These compounds are useful as drugs such as psychotropic agent, antiemetic agent, etc.

10 Claims, No Drawings

ISOXAZOLE DERIVATIVES

TECHNICAL FIELD AND DISCLOSURE OF THE INVENTION

This invention relates to novel isoxazole derivatives having spontaneous locomotor suppressing activity, anti-apomorphine activity, and like activity useful as drugs such as psychotropic agents and antiemetic agents and are represented by the general formula

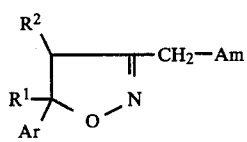

and pharmaceutically acceptable acid addition salts thereof. The invention also relates to a process for preparing these compounds.

In the foregoing formula, Ar represents a phenyl group optionally containing a lower alkoxy group or a halogen atom as a substituent, or a pyridyl group, $R^1$ represents a hydrogen atom, a lower alkyl group or a group represented by Ar, $R^2$ represents a hydrogen atom or alternatively $R^1$ and $R^2$ are bound together and form a carbon-carbon bond, and Am represents an amino residue selected from the group consisting of the following residues:

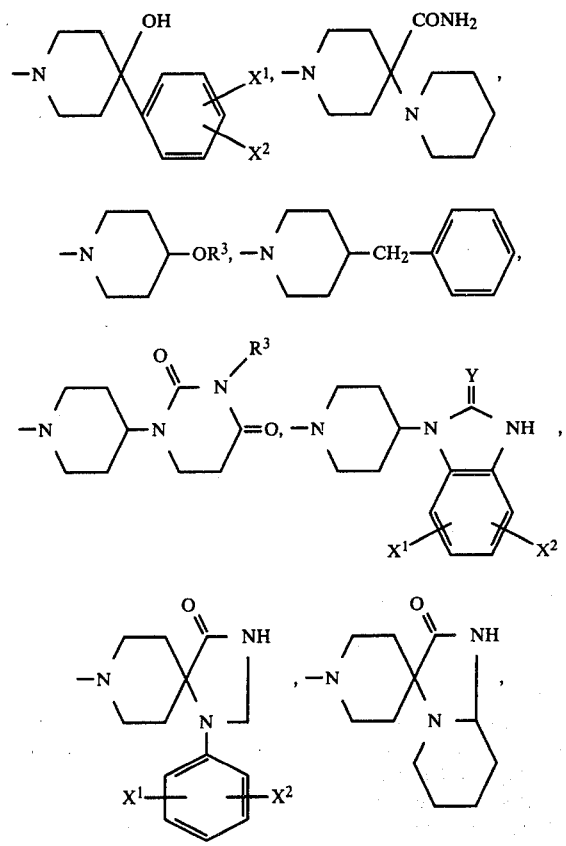

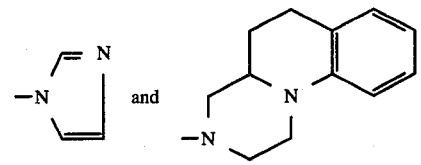

wherein $R^3$ represents a hydrogen atom or a lower alkyl group, $X^1$ and $X^2$ each represent a hydrogen atom, a halogen atom or a trifluoromethyl group, and Y represents O or S.

The term "halogen" herein includes fluorine, chlorine, bromine, etc. The term "lower alkoxy" herein represents a methoxy, ethoxy, propoxy, butoxy, etc. The term "lower alkyl" herein represents methyl, ethyl, propyl, butyl, etc.

The compounds of the formula (I) may be prepared by reacting a compound of the formula

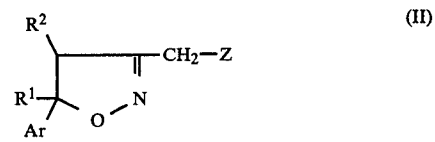

wherein Ar, $R^1$ and $R^2$ are defined as above and Z represents a halogen atom or an organic sulfonyloxy group (e.g. tosyloxy, mesyloxy, etc.), with a compound of the formula $$H-Am \qquad (III)$$

wherein Am is defined as above.

The reaction may be carried out usually in a solvent such as methanol, ethanol, isopropanol, benzene, toluene, xylene, dimethylformamide, chloroform, dichloroethane, acetone, methyl ethyl ketone, etc., at a temperature between room temperature and 140° C., preferably between 50° C. and 110° C., in the presence of potassium carbonate, sodium carbonate, triethylamine or like acid acceptor, for 1 to 48 hours, preferably 4 to 18 hours. The reaction may be accelerated by the use of a catalyst. Examples of such catalyst are potassium iodide, sodium iodide, etc.

The compound of the formula (I) may be converted into an acid addition salt. Typical examples of such an acid addition salt which is pharmaceutically acceptable are salts formed with use of hydrochloric acid, sulfuric acid, phosphoric acid, methanesulfonic acid, maleic acid, oxalic acid, succinic acid, fumaric acid, acetic acid, lactic acid and citric acid.

The experiments carried out for demonstrating anti-apomorphine activity of the compounds of this invention in mice will be described below.

Experimental method:

Groups of 5 male dd-mice (20-25 g body weight) each were used. Apomorphine hydrochloride (0.5 mg/kg) was subcutaneously administered 60 minutes after oral administration of test compound. Immediately after the apomorphine treatment, motor activity was determined for 20 minutes by animex. For the control groups, 0.5% methylcellulose solution was administered instead of test compound. The $ED_{50}$, a dose which inhibited the motor activity by 50% as compared with the control, was determined.

Results:

| Compound | Anti-apomorphine activity ED$_{50}$ (mg/kg, p.o.) |
| --- | --- |
| A | 1.7 |
| B | 2.1 |
| C | 3.4 |
| Clozapine | 10 |

A:1-[5-(4-Fluorophenyl)-4,5-dihydroisoxazol-3-ylmethyl]-4-(2-oxo-1-benzimidazolinyl)piperidine fumarate
B:1-[5-(4-Fluorophenyl)-4,5-dihydroisoxazol-3-ylmethyl]-4-(5-fluoro-2-oxo-1-benzimidazolinyl)piperidine maleate
C:1-[5-(4-Fluorophenyl)-4,5-dihydroisoxazol-3-ylmethyl]-4-(4-chlorophenyl)-4-hydroxypiperidine fumarate The compounds of the formula (II) are novel and may be prepared, for example, by reducing a compound of the formula

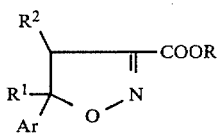

wherein Ar, R$^1$ and R$^2$ are as defined above and R represents a lower alkyl group, with use of sodium borohydride etc., and reacting the resulting compound of the formula

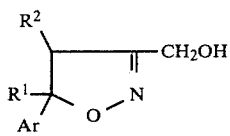

wherein Ar, R$^1$ and R$^2$ are as defined above, with thionyl chloride, phosphorus tribromide or like halogenating agent or tosyl chloride, mesyl chloride or like organic sulfonating agent.

REFERENCE EXAMPLE 1

To a solution of 7 g of ethyl 5-phenyl-4,5-dihydroisoxazol-3-ylcarboxylate in 70 ml of methanol, cooled with ice, is added 1.5 g of sodium borohydride in small portions with stirring. After 4 hours has passed, the solvent is distilled off under reduced pressure and the residue is extracted with ethyl acetate. The extract is washed with water, dried and the solvent is evaporated. The crystalline residue thus obtained is recrystallized from isopropyl ether, giving 3-hydroxymethyl-5-phenyl-4,5-dihydroisoxazole in the form of white crystals. Melting point: 73°–74° C.

REFERENCE EXAMPLE 2

3-Hydroxymethyl-5-phenyl-4,5-dihydroisoxazole (3.2 g) is dissolved in 50 ml of anhydrous ether. To the solution cooled with ice is slowly added dropwise 2.6 g of thionyl chloride with stirring. The reaction mixture is allowed to stand overnight at room temperature and then the solvent is distilled off to give 3-chloromethyl-5-phenyl-4,5-dihydroisoxazole in the form of yellow brown oil.

The compounds of the formula (I) are used in combination with a suitable and conventional pharmaceutically acceptable excipient in the form of a pharmaceutical composition. The pharmaceutical composition may take usual forms such as of tablets, capsules, powders, granules, injection solutions, etc.

When administered for pharmaceutical uses, the compounds of this invention may, for example, be formulated into a pharmaceutical composition as follows.

Tablets (10 mg) may be prepared from the following ingredients:

| Compound (I) or salt thereof | 10 |
| --- | --- |
| Lactose | 53 mg |
| Crystalline cellulose | 15 mg |
| Corn starch | 20 mg |
| Polyvinyl alcohol | 1.5 mg |
| Magnesium stearate | 0.5 mg |
|  | 100 mg |

A compound (I) or salt thereof, crystalline cellulose and corn starch are mixed together and then the mixture is kneaded with 5% polyvinyl alcohol. The resulting mixture is granulated, dried and the dry granules are passed thorough 24-mesh screen. The fine granules are mixed with magnesium stearate to form granules for the preparation of tablets. Tablets are prepared by compressing the granules on punches (6.5 mm, 7.0R).

The dose of the compounds of the formula (I) ranges from 0.005 to 100 mg/kg body weight/day, preferably from 0.01 to 50 mg/kg body weight/day, which may be administered at one time or at several times, although variable depending on the age, body weight and/or severity of the conditions to be treated or response to the medication.

This invention will be better understood from the following examples, which are not to be construed as limitative of the present invention.

EXAMPLE 1

3-Chloromethyl-5-phenyl-4,5-dihydroisoxazole (5.87 g), 6.3 g of 4-(4-chlorophenyl)-4-hydroxypiperidine, 4 g of potassium carbonate and 50 ml of ethanol are heated to 60°–70° C. with stirring for 6 hours. The reaction mixture is filtered and the filtrate is condensed by distillation under reduced pressure. To the residue are added 200 ml of ethyl acetate and 100 ml of water. The organic layer is separated off, washed with water, dried on magnesium sulfate and evaporated under reduced pressure. The residue thus obtained is dissolved in isopropyl ether and alcoholic hydrochloric acid is added to the solution. The crystals thus formed are filtered and then recrystallized from isopropyl alcohol, giving 1-(5-phenyl-4,5-dihydroisoxazol-3-ylmethyl)-4-(4-chlorophenyl)-4-hydroxypiperidine hydrochloride. Melting point: 175°–176° C. (decomposition)

EXAMPLE 2

3-Chloromethyl-5-(4-fluorophenyl)-4,5-dihydroisoxazole (40 g), 52 g of 4-(5-chloro-2-oxo-1-benzimidazolinyl)piperidine, 30 g of potassium carbonate, 15 g of potassium iodide and 1 liter of ethanol are heated to a temperature of 70° to 75° C. with stirring for 48 hours. The reaction mixture is then filtered and the mother liquor is condensed under reduced pressure. To the residue are added 800 ml of chloroform and 500 ml of water and the mixture is stirred. The organic layer is separated off, washed with water and dried on magnesium sulfate, and the solvent is distilled off. To the resulting residue are added 130 ml of acetone and 100 ml of isopropyl ether. The crystals thus precipitated are filtered and recrystallized from a mixture of acetone (400 ml) and isopropyl ether (450 ml), to give 67.5 g of 1-[5-(4-fluorophenyl)-4,5-dihydroxyisoxazol-3-ylmethyl]-4-(5-chloro-2-oxo-1-benzimidazolinyl)piperidine having a melting point of 163° to 164° C. Hydrochloride of this compound melts at 216° C. (decomposition).

A 46.5 g-quantity of the above compound (free base) is dissolved in 200 ml of ethanol, and a solution of 15 g of L-tartaric acid in 200 ml of water is added to the ethanol solution. The resulting mixture is allowed to stand at room temperature. The crystals thus precipitated are recrystallized three times from ethanol-water (6:4) to give tartrate monohydrate as colorless prisms. The tartrate monohydrate is treated with an aqueous solution of sodium bicarbonate to give (−)-1-[5-(4-fluorophenyl)-4,5-dihydroisoxazol-3-ylmethyl]-4-(5-chloro-2-oxo-1-benzimidazolinyl)piperidine. Melting point: 143°–145° C. $[\alpha]_D^{25}$: −108.8 (chloroform).

The (+)-isomer of the above compound is obtained in the same manner as above with use of D-tartaric acid. Melting point: 142°–144° C. $[\alpha]_D^{25}$: +112.6 (chloroform).

EXAMPLE 3

3-Chloromethyl-5-(4-fluorophenyl-4,5-dihydroisoxazole (3.2 g), 3.5 g of 4-oxo-1-phenyl-1,3,8-triazaspiro[4,5]decane, 2.1 g of potassium carbonate and 100 ml of ethanol are refluxed for 7.5 hours with stirring. The resulting reaction mixture is filtered and the mother liquor is concentrated. To the residue obtained is added 100 ml of water and the mixture is extracted with ethyl acetate. The extract is washed with water and dried on magnesium sulfate and the solvent is distilled off under reduced pressure. The resulting residue is dissolved in a small amount of alcohol and alcoholic hydrochloric acid is added to the solution. The crystals thus precipitated are filtered and recrystallized from methanol to give 5-(4-fluorophenyl)-3-(4-oxo-1-phenyl-1,3,8-triazaspiro[4,5]decan-8-ylmethyl)-4,5-dihydroisoxazole hydrochloride. Melting point: 219° C. (decomposition).

The following compounds may be prepared in the same manner as in the preceding Examples.

1-[5-(4-Fluorophenyl)-4,5-dihydroisoxazol-3-ylmethyl]-4-(4-chlorophenyl)-4-hydroxypiperidine
  Melting point of ½ fumarate: 147°–148° C.
1-[5-(4-Fluorophenyl)-4,5-dihydroisoxazol-3-ylmethyl]-4-(2-oxo-1-benzimidazolinyl)piperidine
  Melting point of fumarate: 206° C. (decomp.)
1-[5-(2-Chlorophenyl)-4,5-dihydroisoxazol-3-ylmethyl]-4-(5-chloro-2-oxo-1-benzimidazolinyl)piperidine
  Melting point of hydrochloride: 244° C. (decomp.)
1-[5-(3-Chlorophenyl)-4,5-dihydroisoxazol-3-ylmethyl]-4-(5-chloro-2-oxo-1-benzimidazolinyl)piperidine
  Melting point of maleate: 197° C. (decomp.)
1-[5-(4-Fluorophenyl)-4,5-dihydroisoxazol-3-ylmethyl]-4-(5-fluoro-2-oxo-1-benzimidazolinyl)piperidine
  Melting point of maleate: 201° C. (decomp.)
1-[5-(4-Fluorophenyl)-4,5-dihydroisoxaxol-3-ylmethyl]-4-carbamoyl-4-piperidino-piperidine
  Melting point of dihydrochloride: 234° C. (decomp.)
1-[5-(4-Fluorophenyl)-4,5-dihydroisoxazol-3-ylmethyl]-4-benzylpiperidine
  Melting point of hydrochloride: 184° C.
1-(5-Methyl-5-phenyl-4,5-dihydroisoxazol-3-ylmethyl)-4-(5-chloro-2-oxo-1-benzimidazolinyl)piperidine
  Melting point of maleate: 218° C. (decomp.)
5-Phenyl-3-[4-oxo-1-(4-bromophenyl)-1,3,8-triazaspiro[4,5]-decan-8-ylmethyl]-4,5-dihydroisoxazole
  Melting point of maleate: 221° C. (decomp.)
1-(5-Phenyl-4,5-dihydroisoxazol-3-ylmethyl)-4-hydroxypiperidine
  Melting point of maleate: 115°–119° C.
1'-(5-Phenyl-4,5-dihydroisoxazol-3-ylmethyl)-1,2,3,5,6,7,8,8a-octahydro-2-oxoimidazo[1,2-a]-pyridine-3-spiro-4'-piperidine
  Melting point of dihydrochloride: 223° C. (decomp.)
1-[5-(4-Chlorophenyl)-4,5-dihydroisoxazol-3-ylmethyl]-4-(5-chloro-2-oxo-1-benzimidazolinyl)piperidine
  Melting point of hydrochloride: 230° C. (decomp.)
1-[5-(4-Methoxyphenyl)-4,5-dihydroisoxazol-3-ylmethyl]-4-(5-chloro-2-oxo-1-benzimidazolinyl)piperidine
  Melting point of hydrochloride: 229° C. (decomp.)
1-(5-Phenyl-4,5-dihydroisoxazol-3-ylmethyl)-4-(5-chloro-2-thioxo-1-benzimidazolinyl)piperidine
  Melting point of ½ fumarate: 208°–209° C.
1-(5-Phenyl-4,5-dihydroisoxazol-3-ylmethyl)-4-methoxypiperidine
  Melting point of hydrochloride: 162°–164° C.
1-(5-Phenyl-4,5-dihydroisoxazol-3-ylmethyl)-4-carbamoyl-4-piperidino-piperidine
  Melting point of dihydrochloride: 158° C. (decomp.)
1-(5-Phenyl-4,5-dihydroisoxazol-3-ylmethyl)-4-benzylpiperidine
  Melting point of hydrochloride: 208° C. (decomp.)
1-(5-Phenyl-4,5-dihydroisoxazol-3-ylmethyl)-4-(2-oxo-1-benzimidazolinyl)piperidine
  Melting point of fumarate: 206° C. (decomp.)
1-[5-(2-Pyridyl)-4,5-dihydroisoxazol-3-ylmethyl]-4-(5-chloro-2-oxo-1-benzimidazolinyl)piperidine
  Melting point of maleate: 188° C.
1-(5-Phenyl-4,5-dihydroisoxazol-3-ylmethyl)-4-(5-fluoro-2-oxo-1-benzimidazolinyl)piperidine
  Melting point of hydrochloride: 229° C. (decomp.)
5-(Phenyl-3-(4-oxo-1-phenyl-1,3,8-triazaspiro[4,5]-decan-8-ylmethyl)-4,5-dihydroisoxazole
  Melting point of hydrochloride: 226° C. (decomp.)
1-(5-Phenyl-4,5-dihydroisoxazol-3-ylmethyl)-4-(5-chloro-2-oxo-1-benzimidazolinyl)piperidine
  Melting point of maleate: 204° C. (decomp.)
1-(5-Phenyl-3-isoxazolinylmethyl)-4-(5-chloro-2-oxo-1-benzimimdazolinyl)piperidine
  Melting point of hydrochloride: 250° C. (decomp.)
1-[5-(4-Fluorophenyl)-4,5-dihydroisoxazol-3-ylmethyl]-imidazole
  Melting point of fumarate: 110°–111° C.
1-[5-(2-Pyridyl)-4,5-dihydroisoxazol-3-ylmethyl]-4-(3-methyl-2,4-dioxo-1-hexahydropyrimidinyl)piperidine
  Melting point of maleate: 169° C. (decomp.)
1-(5,5-Diphenyl-4,5-dihydroisoxazol-3-ylmethyl)-4-(5-chloro-2-oxo-1-benzimidazolinyl)piperidine
1-[5-(4-Fluorophenyl)-4,5-dihydroisoxazol-3-ylmethyl]-4-(2-thioxo-1-benzimidazolinyl)piperidine
  Melting point of fumarate: 125° C. (decomp.)
1-(5,5-Diphenyl-4,5-dihydroisoxazol-3-ylmethyl)-4-(2-thioxo-1-benzimidazolinyl)piperidine 1-(5,5-Diphenyl-4,5-dihydroisoxazol-3-ylmethyl)-4-(2-oxo-1-benzimidazolinyl)piperidine
  Melting point: 197°–199° C.
1-(5,5-Diphenyl-4,5-dihydroisoxazol-3-ylmethyl)-4-(5-fluoro-2-oxo-1-benzimidazolinyl)piperidine
1-(5,5-Diphenyl-4,5-dihydroisoxazol-3-ylmethyl)-4-hydroxy-4-(4-chlorophenyl)piperidine
  Melting point: 153°–154° C.

1-[5,5-Bis(4-fluorophenyl)-4,5-dihydroisoxazol-3-ylmethyl]-4-(5-chloro-2-oxo-1-benzimidazolinyl)piperidine Melting point: 199°–200° C.

1-[5,5-Bis(4-fluorophenyl)-4,5-dihydroisoxazol-3-ylmethyl[-4-(2-thioxo-1-benzimidazolinyl)piperidine 1-[5,5-Bis(4-fluorophenyl)-4,5-dihydroisoxazol-3-ylmethyl]-4-(2-oxo-1-benzimidazolinyl)piperidine 1-[5,5-Bis(4-fluorophenyl)-4,5-dihydroisoxazol-3-ylmethyl]-4-(5-fluoro-2-oxo-1-benzimidazolinyl)piperidine 1-[5,5-Bis(4-fluorophenyl)-4,5-dihydroisoxazol-3-ylmethyl]-4-hydroxy-4-(4-chlorophenyl)piperidine Melting point: 163°–164° C.

1-[5-(4-Fluorophenyl)-4,5-dihydroisoxazol-3-ylmethyl]-4-(4-chloro-3-trifluoromethylphenyl)-4-hydroxypiperidine 3-[5-(4-Fluorophenyl)-4,5-dihydroisoxazol-3-ylmethyl]-2,3,4,4a,5,6-hexahydro-1H-pyrazino-[1,2-a]-quinoline Melting point of oxalate: 148° C. (decomp.)

While the invention has been described in detail and with reference to specific embodiments thereof, it is apparent that various alterations and modifications can be made without departing from the spirit and scope thereof.

We claim:

1. An isoxazole represented by the formula

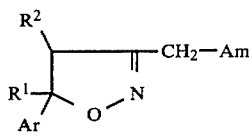

or salts thereof wherein Ar represents a phenyl group which may optionally be substituted with a halogen atom or a lower alkoxy group, or a pyridyl group, $R^1$ represents a hydrogen atom, a lower alkyl or a group represented by a group Ar, $R^2$ represents a hydrogen atom, or alternatively $R^1$ and $R^2$ are bound together and form a carbon-carbon bond, and Am represents an amino residue selected from the group consisting of the following residues:

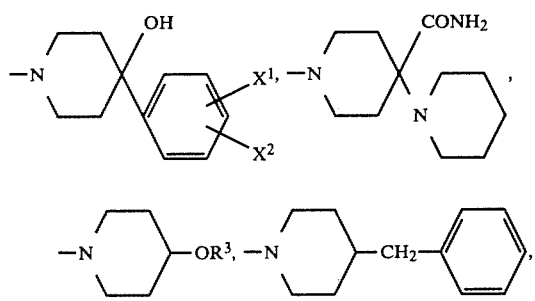

-continued

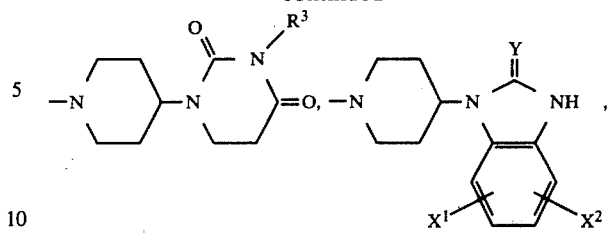

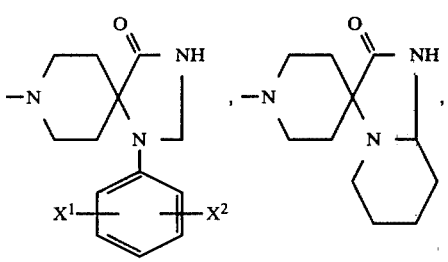

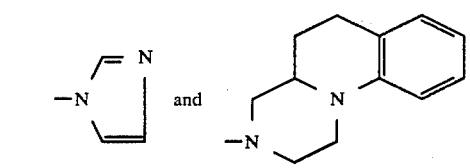

wherein $R^3$ represents a hydrogen atom or a lower alkyl group, $X^1$ and $X^2$ each represent a hydrogen atom, a halogen atom or a trifluoromethyl group and Y represents O or S.

2. The compound of claim 1: 1-[5-(4-Fluorophenyl)-4,5-dihydroisoxazol-3-ylmethyl]-4-(5-chloro-2-oxo-1-benzimidazolinyl)piperidine.

3. The compound of claim 1: 1-[5-(4-Fluorophenyl)-4,5-dihydroisoxazol-3-ylmethyl]-4-(2-oxo-1-benzimidazolinyl)piperidine.

4. The compound of claim 1: 1-[5-(4-Fluorophenyl)-4,5-dihydroisoxazol-3-ylmethyl]-4-(5-fluoro-2-oxo-1-benzimidazolinyl)piperidine.

5. The compound of claim 1: 1-[5-(4-Fluorophenyl)-4,5-dihydroisoxazol-3-ylmethyl]-4-(4-chlorophenyl)-4-hydroxypiperidine.

6. The compound of claim 1: 5-(4-Fluorophenyl)-3-(4-oxo-1-phenyl-1,3,8-triazaspiro-[4,5]-decan-8-ylmethyl)-4,5-dihydroisoxazole.

7. The compound of claim 1: 1-[5-(4-Fluorophenyl)-4,5-dihydroisoxazol-3-ylmethyl]-4-(2-thioxo-1-benzimidazolinyl)piperidine.

8. The compound of claim 1: 1-(5-Phenyl-4,5-dihydroisoxazol-3-ylmethyl-4-(5-chloro-2-thioxo-1-benzimidazolinyl)piperidine.

9. A psychotropic composition comprising a compound of claim 1 in combination with a pharmaceutically acceptable excipient, said compound being present in a psychotropically effective amount.

10. An antiemetic composition comprising a compound of claim 1 in combination with a pharmaceutically acceptable excipient, said compound being present in an antiemetically effective amount.

* * * * *